United States Patent
Smith et al.

(10) Patent No.: US 8,263,115 B2
(45) Date of Patent: *Sep. 11, 2012

(54) METHOD AND A PRODUCT TO REDUCE AND TREAT PROBLEMS ASSOCIATED WITH TINEA PEDIS

(75) Inventors: Jan G. Smith, Askim (SE); Mattias Andrup, Kullavik (SE)

(73) Assignee: Abigo Medical AB, Askim (SE)

( * ) Notice: Subject to any disclaimer, the term of this patent is extended or adjusted under 35 U.S.C. 154(b) by 115 days.

This patent is subject to a terminal disclaimer.

(21) Appl. No.: 12/584,614

(22) Filed: Sep. 9, 2009

(65) Prior Publication Data

US 2010/0062044 A1    Mar. 11, 2010

Related U.S. Application Data

(60) Provisional application No. 61/191,680, filed on Sep. 11, 2008.

(51) Int. Cl.
*A61F 13/00* (2006.01)
*A61F 15/00* (2006.01)
*B29C 65/00* (2006.01)

(52) U.S. Cl. .............. 424/443; 602/47; 602/44; 602/45; 602/56; 602/42; 128/888; 156/250

(58) Field of Classification Search ................. 424/443; 602/47, 44, 45, 56, 42; 128/888; 156/250
See application file for complete search history.

(56) References Cited

U.S. PATENT DOCUMENTS

| | | | |
|---|---|---|---|
| 4,211,227 A | 7/1980 | Anderson et al. | |
| 4,275,721 A | 6/1981 | Olson | |
| 4,617,326 A * | 10/1986 | Bjornberg et al. | 428/536 |
| 4,642,108 A | 2/1987 | Sustmann | |
| 4,643,180 A | 2/1987 | Feld et al. | |
| 4,643,181 A | 2/1987 | Brown | |
| 4,655,756 A | 4/1987 | Fawkes | |
| 4,678,704 A | 7/1987 | Fellows | |
| 4,832,009 A | 5/1989 | Dillon | |
| 5,380,294 A | 1/1995 | Persson | |
| 5,447,492 A | 9/1995 | Cartmell et al. | |
| 5,464,610 A | 11/1995 | Hayes, Jr. et al. | |
| 5,497,789 A | 3/1996 | Zook | |
| 5,498,416 A | 3/1996 | Carsenti-Etesse et al. | |
| 5,700,742 A | 12/1997 | Payne | |
| 5,707,736 A | 1/1998 | Levy et al. | |
| 5,753,256 A | 5/1998 | Cordes et al. | |
| 5,817,325 A | 10/1998 | Sawan et al. | |

(Continued)

FOREIGN PATENT DOCUMENTS

DE    100 20 989 A1    4/2000

(Continued)

*Primary Examiner* — Blessing Fubara
(74) *Attorney, Agent, or Firm* — Lynn E. Barber

(57) ABSTRACT

A ring-shaped toe-patch is provided for treatment and prevention of *tinea pedis*, commonly known as athlete's foot. The toe-patches are made of rubber-foam, attached to a hydrophobic material for elimination of fungus like *T. rubrum*. The toe-patch has cuts extending into the patch from the central circle in the toe-patch. Due to its perfect fit the toe-patch comes close to the affected area making it possible for a hydrophobic material attached to foam to effectively bind the fungi. Simultaneously with the elimination of the fungi the toe-patch works as a toe separator creating space between the toes.

19 Claims, 1 Drawing Sheet

U.S. PATENT DOCUMENTS

| | | |
|---|---|---|
| 5,856,248 A | 1/1999 | Weinberg |
| 5,941,840 A | 8/1999 | Court et al. |
| 6,037,431 A | 3/2000 | Shioji et al. |
| 6,160,196 A | 12/2000 | Knieler et al. |
| 6,369,289 B1 | 4/2002 | Orr, III |
| 6,416,779 B1 | 7/2002 | D'Augustine et al. |
| 7,576,256 B2 | 8/2009 | Bjornberg et al. |
| 2003/0068331 A1 | 4/2003 | Battaglia et al. |
| 2004/0082925 A1 | 4/2004 | Patel |
| 2004/0127831 A1 | 7/2004 | Sigurjonsson |
| 2004/0161452 A1 | 8/2004 | Petit |
| 2004/0265362 A1 | 12/2004 | Susilo |
| 2006/0163149 A1 | 7/2006 | Wadstrom et al. |
| 2006/0165761 A1 | 7/2006 | Trotter |
| 2006/0264857 A1 | 11/2006 | Colbert |
| 2008/0177214 A1 | 7/2008 | Robertsson et al. |
| 2008/0249485 A1 | 10/2008 | Effing |

FOREIGN PATENT DOCUMENTS

| | | |
|---|---|---|
| EP | 0 475 807 A2 | 3/1992 |
| WO | WO 92/13577 | 8/1992 |
| WO | WO 2004/017881 A1 | 3/2004 |
| WO | WO 2005/067991 A1 | 7/2005 |
| WO | WO 2007/062024 A1 | 5/2007 |
| WO | WO 2007/073246 A1 | 6/2007 |

* cited by examiner

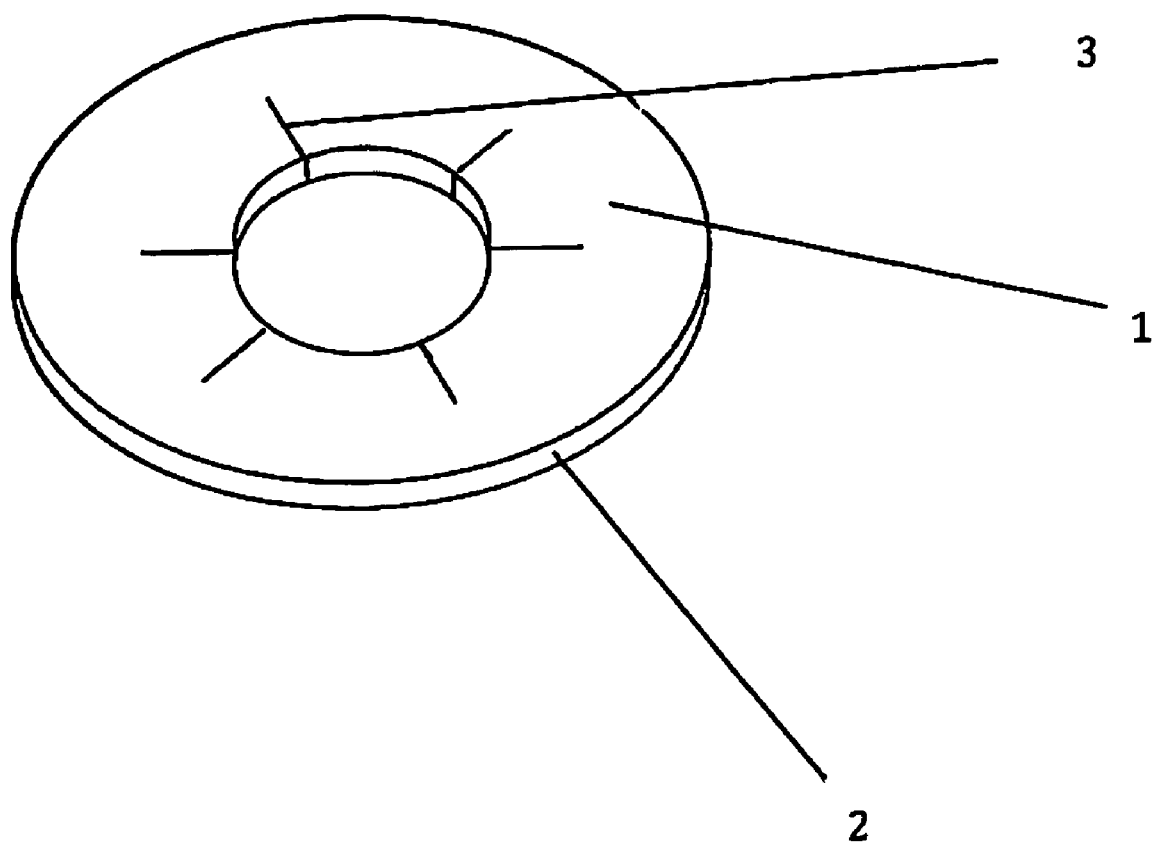

METHOD AND A PRODUCT TO REDUCE AND TREAT PROBLEMS ASSOCIATED WITH TINEA PEDIS

CROSS-REFERENCE TO RELATED APPLICATIONS

This application claims priority from U.S. Provisional Application, Ser. No. 61/191,680, filed Sep. 11, 2008.

FIELD OF THE INVENTION

The invention herein relates to a toe-patch, for treatment and prevention of tinea pedis, commonly known as athlete's foot. More specifically the invention relates to a toe-patch that due to its perfect fit comes close to the affected area, making it possible for a hydrophobic material attached to foam to effectively bind to the fungi that cause tinea pedis. Simultaneously with the elimination of the fungi, the toe-patch works as a toe separator creating space between the toes.

BACKGROUND OF THE INVENTION

According to the hydrophobic principle of the laws of nature, a system will always struggle towards lowest possible energy consumption. When two water repellent molecules come into collision with each other they will increase the entropy and create disorder. The water molecules that surround the two hydrophobic molecules will force them together by hydrogen bonds between the water molecules although there is no force of attraction between the hydrophobic molecules, and will expel the water molecules.

Numerous studies during the last few decades have shown that bacteria, the yeast *Candida albicans* and the fungus *Trichophyton rubrum* commonly express profound cell surface hydrophobicity. Several structures which render the cell surface hydrophobic have been defined, like the fimbriae of *Escherichia coli* which mediate adhesion to the intestinal wall, proteins on *Candida albicans* and *T. rubrum* which have been called "hydrophobins", and lipoteichoic acid in the cell wall of Gram-positive bacteria.

The initial step of infections of the skin and mucosal surfaces is microbial adhesion to wounded tissues. Several microbial components that adhesively bind to specific receptors have been identified. Initial adhesion can be mediated by hydrophobic interactions between microbes and host tissue structures, and also by charge interactions. Binding of extracellular matrix and serum proteins, like fibronectin, collagen and fibrinogen may further enhance colonization of deeper wound tissue. Utilizing the SORBACT® principle described in patent application WO2006062470, assigned to the same group as the instant invention, products such as the SORBACT® pad consist of folded acetate gauze and cotton gauze treated with the fatty acid ester DACC (dialkyl carbamoyl chloride). This provides SORBACT® pads with a strong hydrophobic property. When the SORBACT® pad comes into contact with pathogenic microorganisms in the wound surface, the microorganisms adhere to the pad through hydrophobic interaction. The method is based on the principle that two hydrophobic surfaces bind to each other, when coming into physical contact. The SORBACT® pad consists of two components. The first component has one or more liquid permeable layers of a hydrophobic, bacteria-adsorbing, physiologically innocuous material containing a woven or nonwoven hydrophilic fabric. The fabric has been rendered hydrophobic by chemical treatment with a compound containing hydrophobic groups. The second component consists of one or more layers of a hydrophilic, liquid adsorbing, physiologically innocuous material. The hydrophilic liquid absorbing material affects a liquid flow by suction of exudate from the wound. If the microorganisms exhibit hydrophobic surface structures they will accompany this flow of liquid and come in contact with the hydrophobic component and bind to it.

Another antimicrobial property of the SORBACT® product is its cation activity. The exterior membranes of mammalian cell exterior membranes are generally neutral. Thus the positively charged SORBACT® material preferentially binds to membranes of microorganisms (negatively charged) and lifts them away. U.S. patent application Ser. No. 10/559,464 (publication number 2006/0163149) relates to a product for absorption, whereby a hydrophobic entity and a positively charged entity are connected to a support matrix. In this method, the hydrophobic entity may be connected by using DACC, and the positively charged entity may be connected by using polyethyleneimine. Preferred fields of the prior application are filters, face masks, wound dressings, nasal sprays, and drapes for use during surgical intervention etc. However unlike the invention herein they do not mention treatment of athlete's foot nor attachment of a hydrophobic material to foam or the like.

Athlete's foot is a common name given to a fungal infection of the skin that predominately occurs between the toes but can occur anywhere on the foot. The term athlete's foot is a highly misleading word, as this condition does not only occur in athletes. It is caused by one of four dermatophytes, the most common being *Trichophyton rubrum*, which is a microscopic fungus that lives on dead tissue of the hair, toenails, and outer skin layers. The fungus thrives in warm, moist environments including shoes, socks, and the floors of public showers, locker rooms, and swimming pools. Athlete's foot is transmitted through contact with a cut or abrasion on the plantar surface (bottom) of the foot. The infection causes raised, circular pimples or blisters.

There are four common forms of athlete's foot. The most common is a persistent itching of the skin on the sole of the foot or between the toes. As the infection progresses, the skin grows soft. The center of the infection is inflamed and sensitive to the touch. Gradually, the edges of the infected area become milky white and the skin begins to peel. There may also be a slight watery discharge.

The second presentation is the ulcerative type. In this presentation, the peeling skin becomes worse. Large cracks develop in the skin, making the patient susceptible to secondary bacterial infections. The infection can be transmitted to other parts of the body by scratching or contamination of clothing or bedding.

The third type of infection is often called "moccasin foot." In this type, a red rash spreads across the lower portion of the foot in the pattern of a moccasin. The skin in this region gradually becomes dense, white, and scaly.

Finally, the fourth form of *tinea pedis* is inflammatory or vesicular, in which a series of raised bumps or ridges develops under the skin on the bottom of the foot, typically in the region of the metatarsal heads. Itching is intense and there is less peeling of the skin.

People with acute tinea infections may develop similar outbreaks on their hands, typically on the palms. This trichophyde reaction, also known as tineas manuum, is an immune system response to fungal antigens (antibodies that fight the fungal infection).

Tinea pedis has proven difficult to eliminate and often recurs. Infections may disappear spontaneously or persist for years. Best results usually are obtained with early treatment before the fungal infection establishes itself firmly. Historically, antifungal drugs have been used. For early "mild" cases, Imidazole class drugs are used to combat fungal infections by attacking the enzymes of the fungal cell walls, inhibiting growth and reproduction. Examples of these drugs include clotrimazole (LOTRIMIN®) and miconazole (contained in LOTRIMIN® and ABSORBINE JR.®). They are applied topically and massaged into the skin. They must be reapplied every few hours over a period of weeks.

More difficult cases may require the use of the allylamines class of drugs. These drugs include terbinafine (contained in LAMISIL®) and naftifine (NAFTIN®) and are available in non-prescription form. The most difficult cases must be treated with drugs such as griseofulvin (FULVICIN® and GRISACTIN®) and concentrated forms of terbinafine and itraconazole. Griseofulvin can cause side effects such as headache, nausea, and numbness, so it is used as a last resort.

These treatments are not without shortcomings. The topical treatments require use for many days, if not weeks. Often the condition occurs on the skin areas of the feet that that come into frequent frictional contact with a patient's clothing or with other skin surfaces. As a result of this frictional contact, topically applied medications can be more easily removed from the affected areas of a patient's foot. Moreover, topically applied medications are more prone to the effects of moisture that is present at the affected area of skin. These difficulties mean that treatment is significantly reduced, because the medication is not held in place for a sufficient time. As a result, the efficacy of the treatment is significantly reduced, and patients must frequently reapply medications so that the affected area receives proper treatment. Furthermore, the inconvenience of bandages due to constant or frequent movement and flexing of the skin, the small surface area usually involved (such as the toes), friction and moisture, make bandages impractical for minimizing frictional contact that occurs at the affected areas of a patient's foot, as well as impractical as a means to hold the medication in place for longer periods of time. In other words, the topical medications are messy creams and lotions. When it comes to internal drugs, the issue is that they can cause side effects, including headaches, nausea, and in extreme cases, organ damage.

Patches for treatment of athlete's foot are not previously described in literature while band-aids for the treatment of toe and finger nail fungus infections are known, for instance, WO-A-99/40955, U.S. Pat. No. 5,753,256 and US patent applications US20040265362, US20040161452 and U.S. Pat. No. 5,464,610.

The invention described in US patent application 20030068331 relates to gum resin or other film forming agent-based biological dressings that adhere to the skin and contain one or more pharmacologically active agents for the treatment of symptoms relating to athletes foot. The biological dressing comprises a sticky film of gum resin or other agent which forms a film on the skin and a pharmacologically active agent. This is in contrast to the invention herein where the dressing is ring-shaped or dog-bone shaped, non-sticky and removable. Furthermore the invention herein does not comprise any pharmacologically active agents, since the efficacy is due to hydrophobic action in combination with the separation of toes.

There are many different types of toe separators commercially available from foot care manufacturers. These are usually made of variously shaped pieces of soft silicon, felt or foam material that may be impregnated with soothing oils or aromatic substances. These are placed separately between the toes that chafe each other to prevent the interdigital fiction. They can be ring-shaped as in the invention herein but the toe separators are only used for separation of the toes. They only get the drying effect and not both the drying and the removal of the fungus.

Circular cushions are known for placement over calluses, for example "Round Callus Cushions", sold by DR. SCHOLL'S®. Unlike the invention herein such cushions are not mounted with foam material with a hydrophobic fabric attached thereto, nor are they meant to be placed around a toe.

There are a number of patents and patent applications describing drying appliances for preventing athlete's foot e.g, DE 10020989, U.S. Pat. No. 3,943,922 A, and U.S. Pat. No. 5,497,789. However unlike the invention herein the anti-fungal effect is due to drying between the toes by separators not due to elimination of microbes by the hydrophobic effect.

Patent application WO2004017881 discloses a moisture-absorbing soft sleeve to be passed on the toe for treating athlete's foot. The sleeve is made of wood or cotton. The disadvantage of the invention is that the sleeve is only efficient when dry. Under moisture conditions, unfortunately, the microbes are able to multiply.

Therefore, there is a need for an alternative athlete's foot treatment without using antimicrobial substances, that due to a perfect fit remains at the treatment site for a sufficient period, that reduces the spread or transmission of the fungal infection, and that provides fast, effective relief from the symptoms of athlete's foot.

The inventors herein surprisingly discovered that a ring-formed toe-patch consisting of a hydrophobic material with a foam-layer described in patent application US2008/0177214 met this need. The invention is not limited to just a ring-formed product but relates to all toe-patches consisting of a hydrophobic material with a foam-layer cut to have a perfect fit around a *tinea pedis* affected area, for example dogbone-shaped toe-patches.

Due to the perfect fit the product of the invention herein can come close to the affected area for an effective treatment. Simultaneously with the elimination of the fungus it works as a toe separator creating space between the toes, so that the attacked area will be aired and dried up. The use of the moisture-absorbent foam attached to the hydrophobic material increase the drying effect. This material was disclosed by the inventors of the invention herein and described in US 2008/0177214. In contrast to the topically applied medications on the market that are more prone to the effects of moisture the invention herein provides a significantly more effective treatment of athlete's foot.

The product is held on place by normal socks and may be used together with ordinary footwear. Accordingly, the patient can be spared of the inconvenience of bandages due to movement, friction and moisture.

Furthermore, because the treatment and prevention methods of the present invention provide a stronger physical barrier at the affected skin area, the risks of spread or transmission of the fungal infection, either to other areas of the patient's body or to other individuals is significantly decreased. The present invention thus provides significant public health benefits.

BRIEF DESCRIPTION OF THE DRAWINGS

FIG. 1 is a perspective view of a ring-shaped toe-patch according to the invention herein.

SUMMARY OF THE INVENTION

The invention herein provides a treatment that helps to alleviate *tinea pedis* and is safe and easy to use. It is yet another object of the present invention to provide a treatment using circular toe-patches made of rubber-foam, attached to a hydrophobic material and for elimination of fungus like *T. rubrum*. The toe-patch of the invention is ring-shaped and has cuts extending into the patch from the central circle in the toe-patch. Objects and features of the inventions will be more fully apparent from the following disclosure and appended claims.

DETAILED DESCRIPTION OF THE INVENTION AND PREFERRED EMBODIMENTS THEREOF

The product of the invention is ideal for treatment of *tinea pedis*. It reduces the number of the fungus *T. rubrum* without using antimicrobial substances. The product of the invention consists of two bonded layers: hydrophobic cellulose acetate fabric that binds microorganisms and an attached rubber-foam layer.

The toe-patch device of the invention for treating and preventing *tinea pedis*, comprises a hydrophobic layer, attached to a foam layer to form a toe-patch. Each toe-patch is circular with an outer diameter, and has a central circle cut through the hydrophobic layer and the attached foam layer. A plurality of cuttings extends into the toe-patch at regular intervals around the central circle.

Referring now to the FIGURE, FIG. 1 shows the hydrophobic layer (1), and the foam layer (2), and the cuttings (3). The cuttings are preferably made at 6 locations, at regular intervals. Each cut (3) is preferably 6 mm long. When placed on the toe the cuttings allow the toe-patch to fit closer to the skin. The cuttings also make the product adjustable to different thickness of toes.

The hydrophobic layer (1) is placed towards the area of the infection. The hydrophobic material may comprise, for example, a hydrophobic fabric or hydrophobic non-woven fabric that has been rendered hydrophobic by a special treatment, or a hydrophobic, perforated foil. Hydrophobic woven and non-woven fabrics may be produced from synthetic fibers or the type polyamide, polypropylene and polytetrafluoroethylene fibers, or from carbon fibers. In order to obtain a hydrophobic material from a woven or non-woven hydrophilic fabric, such as woven or non-woven cotton fabric, the fabric may be treated chemically for example, in a known manner, with a compound containing hydrophobic groups, for example with a DACC (dialkyl carbamoyl chloride) such as dihexadecyl-carbamoyl chloride or dioctadecyl-carbamoyl chloride or an alkyl ketene dimer (AKD).

A preferred hydrophobic layer of the invention is made of green cellulose acetate to which dialkyl carbamoyl chloride is applied as discussed in the examples.

The hydrophobic layer is attached to the foam layer with the aid of a suitable adhesive, for example 9L8 (Protechnic Sweden). Other adhesives known in the art could also be used. The foam can be based on for example polyether, polyester and cellulose.

The fungi will be removed when the dressing is changed. Hence, the number of microorganisms decreases over time to a number that the body can control and the wound can heal. Since microbes adhere to the dressing by hydrophobic interactions, spread of microorganisms to the environment during changing of dressings is limited. With this method, the fungal load of the affected surface is reduced rapidly and effectively. The body's own defense mechanism can then take over, and the natural healing process can continue. The use of the hydrophobic layer, even without systemic antibiotic therapy, decreases the number of infecting fungus but does not eliminate all bacteria, which is an advantage since a small number of microorganisms stimulate the healing. The invention replaces the use of topical medicaments and hence reduces the spread of resistant organisms.

An alternative method to lift the microbes from for example a wound is the electrostatic solution for example a positively charged entity, such as described in U.S. Patent application 2006/0163149. The positively charged entity is used together with the foam layer. A further method to lift the microbes is to use the hydrophobic method in combination with the electrostatic method together with the foam-layer.

Other objects and features of the inventions will be more fully apparent from the following examples and appended claims.

EXAMPLE 1

Manufacture of Wound Dressing Product with Foam as the Moisturizing Matrix

In this example a ring-formed toe-patch is manufactured based on the invention in the following manner:
Materials:

| LAYER | COMMERCIAL PRODUCT NAME | MANUFACTURER |
| --- | --- | --- |
| 1. Hydrophobic layer | Green Cellulose Acetate woven prepared according to U.S. Pat. No. 4,617,326 | ABIGO Medical AB Sweden |
| 2. Adhesive | 9L8 | Protechnic, France |
| 3. Moisturizing foam | Vivo PCF 03 | Corpura, Holland |

The hydrophobic layer is preferably produced according to U.S. Pat. No. 4,617,326 by applying to a cellulose acetate fabric an amount of dialkyl carbamoyl chloride as disclosed in this patent making a covalent bond between the materials.

The acetate fabric is on rolls at a width of 1 m, and taken as such to the next step.

The adhesive component is applied to the foam material by using pressure (maximum 5 bar) at a temperature of maximum 90° C. and at an amount of <30 g/m$^2$, preferably at 20 g/m$^2$.

The now bonded hydrophobic layer (1) and foam layer (2) is punched into suitable size pieces for the final product. The toe-patch is punched in a circular form, preferably 4.2 cm diameter. In the center of the circular patch, a 1.2 cm circle is punched out, giving the patch the form of a ring. From the inner side, the ring is punched at 6 locations, resulting in 6 cuts (3) at regular intervals. Each cut (3) is 6 mm long. The product is sterilized (Isotron Gamma Irradiation, Netherlands).

EXAMPLE 2

Prospective Study on the Topical Treatment of Interdigital Fungal Infections in Diabetic Patients Twenty diabetic patients were admitted to this open prospective study, by a chiropodist in diabetic care at the diabetic foot clinic at the hospital NÄL in Sweden. The patients were included in regularly planned follow ups with the chiropodist. Inclusion criteria were clinically identified topical interdigital fungal infections. The patients were treated once daily using the ring-formed toe-patch, manufactured by Abigo Medical AB, Sweden.

At the patient's first visit to the clinic, bedside assessment of the infection was performed, and swabs for culturing and photos of the infected areas were taken. The toe-patch was applied by the investigator and the patients were carefully instructed how to do the application and handle the foot hygiene by themselves between the controls. The patients were admitted back to the clinic at day 5 and 10 for bedside evaluation, culturing for fungi and photo documentation.

Results:

The evaluation was through photographs by blinded independent observer according to protocol. Clinical and visual evaluation were done bedside and through photographs according to a preset evaluation protocol. All twenty patients completed the study. No side effects were noted.

Microbiology. Culture for fungus was taken at day 1, 5 and 10. The microbiology findings showed a broad variation of different fungus present in the treated area: *Trichophyton, Penicillium, Fusarium, Trichosporon, Dermathophyts* and *Candida*.

Photo evaluation. Pictures of the lesion where taken at day 1, 5 and 10 by the investigator and blind evaluation was performed by an independent investigator, shown in table 1.

TABLE 1

| Assessment | Day 5 | Day 10 (%) |
|---|---|---|
| Deteriorated | 2 patients | 1 patient (5) |
| Unchanged | 7 patients | 4 patients (20) |
| Improved | 11 patients | 5 patients (25) |
| Healed | 0 patients | 10 patients (50) |
| Not assessable | 0 patients | 0 patients (0) |

Seventy five percent (75%) of the patients were improved or healed after ten days of treatment. Twenty percent (20%) were unchanged and five percent (5%) deteriorated Table 1. After 10 days the healed patients had negative fungal cultures.

The investigator found the ring-formed toe-patch very easy to use in all patients.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A device for treating *tinea pedis*, comprising:
    a) a hydrophobic layer, attached to a foam layer to form a toe-patch, wherein each toe-patch is circular with an outer diameter, and has a central circle cut through the hydrophobic layer and the attached foam layer; and
    b) a plurality of cuttings extending into the toe-patch at regular intervals around the central circle.

2. The device of claim 1, wherein the hydrophobic layer is made of a material selected from the group consisting of: a) a hydrophobic woven fabric or hydrophobic non-woven fabric that has been rendered hydrophobic by a chemical treatment with a compound containing hydrophobic groups, and b) a hydrophobic, perforated foil.

3. The device of claim 2, wherein the material is a fabric that has been rendered hydrophobic by a chemical treatment with a dialkyl carbamoyl chloride or an alkyl ketene dimer.

4. The device of claim 3, wherein the dialkyl carbamoyl chloride is selected from the group consisting of dihexadecyl-carbamoyl chloride and dioctadecyl-carbamoyl chloride.

5. The device of claim 1, wherein the hydrophobic layer is made of synthetic fibers selected from the group consisting of polyamide fibers, polypropylene fibers, polytetrafluoroethylene fibers, and carbon fibers.

6. The device of claim 1, wherein the hydrophobic layer is made of green cellulose acetate to which dialkyl carbamoyl chloride has been applied.

7. The device of claim 1, wherein the foam layer comprises a foam made of a material selected from the group consisting of polyether, polyester and cellulose foams.

8. The device of claim 1, wherein cuttings are made at six locations, at regular intervals.

9. The device of claim 8, wherein each cut is 6 mm long.

10. The device of claim 1, wherein the hydrophobic material is bonded to the foam layer with an adhesive.

11. A method of making a device according to claim 1 for treating *tinea pedis*, comprising:
    a) providing a hydrophobic layer;
    b) bonding the hydrophobic layer to a foam layer with an adhesive to form a bonded layer;
    c) punching the bonded layer into at least one circular toe-patch;
    d) punching a central circle in each circular toe-patch;
    e) cutting a plurality of cuts in each circular toe-patch, each of the cuts extending from the central circle, the cuts on each toe-patch being placed at regular intervals around the central circle; and
    f) sterilizing the toe-patches.

12. The method of claim 11, further comprising making the hydrophobic layer by applying to a cellulose acetate fabric an amount of dialkyl carbamoyl chloride to make a covalent bond between the cellulose acetate fabric and the dialkyl carbamoyl chloride.

13. The method of claim 11, wherein the cellulose acetate fabric is on rolls having a width of 1 m.

14. The method of claim 11, wherein a plurality of toe-patches is cut from each bonded layer.

15. The method of claim 11, wherein there are six cuts in each device.

16. The method of claim 11, wherein each device has an outer diameter of about 4.2 cm, each central circle has a diameter of 1.2 cm, and each cut is 6 mm long.

17. The method of claim 11, wherein the adhesive component is applied to the foam layer using pressure at a temperature of maximum 90° C. and at an amount of less than 30 g/m$^2$.

18. A method for treating *tinea pedis*, comprising:
    a) providing a device made according to claim 11; and
    b) applying the device to an area of a foot to reduce the number of fungi without using antimicrobial substances and without requiring adhesive to hold the device to the foot.

19. The method of claim 18, wherein the fungus is *Trichophyton rubrum*.

* * * * *